(12) United States Patent
Smisson, III et al.

(10) Patent No.: US 8,668,725 B2
(45) Date of Patent: Mar. 11, 2014

(54) BONE SCREW

(75) Inventors: Hugh F. Smisson, III, Macon, GA (US);
David C. Field, Snellville, GA (US);
Paul Gombar, Jr., Winder, GA (US);
Walter R. Sanders, Duluth, GA (US);
Brandi Bohleber, Macon, GA (US)

(73) Assignee: Southern Spine, LLC, Macon, GA (US)

( * ) Notice: Subject to any disclaimer, the term of this patent is extended or adjusted under 35 U.S.C. 154(b) by 1017 days.

(21) Appl. No.: 11/777,832

(22) Filed: Jul. 13, 2007

(65) Prior Publication Data
US 2009/0018589 A1 Jan. 15, 2009

(51) Int. Cl.
*A61B 17/86* (2006.01)
*A61B 17/80* (2006.01)

(52) U.S. Cl.
USPC .................. 606/317; 606/315; 606/286

(58) Field of Classification Search
USPC .......... 606/286, 301, 309–312, 315–318; 411/307, 411–415, 423
See application file for complete search history.

(56) References Cited

U.S. PATENT DOCUMENTS

| | | | |
|---|---|---|---|
| 4,640,271 A | 2/1987 | Lower | |
| 4,854,311 A | 8/1989 | Steffee | |
| 4,957,496 A | 9/1990 | Schmidt | |
| 4,957,497 A | 9/1990 | Hoogland et al. | |
| 5,019,079 A | 5/1991 | Ross | |
| 5,098,434 A | 3/1992 | Serbousek | |
| 5,180,382 A | 1/1993 | Frigg et al. | |
| 5,209,753 A | 5/1993 | Biedermann et al. | |
| 5,334,204 A | 8/1994 | Clewett et al. | |
| 5,403,136 A * | 4/1995 | Mathys | 411/310 |
| 5,456,685 A * | 10/1995 | Huebner | 606/321 |
| 5,474,555 A | 12/1995 | Puno et al. | |
| 5,492,442 A | 2/1996 | Lasner | |
| 5,549,612 A | 8/1996 | Yapp | |
| 5,562,672 A | 10/1996 | Huebner | |
| 5,571,139 A * | 11/1996 | Jenkins, Jr. | 606/232 |
| 5,601,553 A * | 2/1997 | Trebing et al. | 606/86 B |
| 5,735,853 A | 4/1998 | Olerud | |
| 5,743,914 A | 4/1998 | Skiba | |
| 5,766,254 A | 6/1998 | Gelbard | |
| 5,792,142 A * | 8/1998 | Galitzer | 606/65 |
| 5,797,909 A | 8/1998 | Michelson | |
| 5,797,911 A | 8/1998 | Sherman et al. | |
| 5,797,914 A * | 8/1998 | Leibinger | 606/308 |
| 5,843,082 A | 12/1998 | Yuan | |
| 5,871,486 A | 2/1999 | Huebner | |
| 5,876,435 A * | 3/1999 | Swords et al. | 623/4.1 |

(Continued)

FOREIGN PATENT DOCUMENTS

FR 2855391 A1 * 12/2004 ............ A61B 17/68
WO WO2004/006792 1/2004

*Primary Examiner* — Michael T Schaper
(74) *Attorney, Agent, or Firm* — Sutherland Asbill & Brennan LLP

(57) ABSTRACT

A bone screw is provided for securing a medical device to bone. The bone screw can engage with a bone screw hole in a medical device, such as an anterior cervical plate or sternal closure plate. Embodiments of the bone screw can include a screw head, a smooth cylindrical shaft region, a first and a second cylindrical shaft region with external threading, a tapered shaft region with external threading and one or more recessed flutes, and a sharp tip without threading or fluting. The external threading in the first and the second cylindrical shaft regions can have different pitches and crests. The external threading on the tapered shaft region can be tapered.

35 Claims, 3 Drawing Sheets

(56) References Cited

U.S. PATENT DOCUMENTS

| | | | |
|---|---|---|---|
| 5,879,350 A | 3/1999 | Sherman et al. | |
| 5,885,286 A | 3/1999 | Sherman et al. | |
| 5,925,048 A | 7/1999 | Ahmad | |
| 5,951,558 A | 9/1999 | Fiz | |
| 5,964,768 A | 10/1999 | Huebner | |
| 5,989,255 A | 11/1999 | Pepper et al. | |
| 6,016,727 A | 1/2000 | Morgan | |
| 6,030,162 A * | 2/2000 | Huebner | 411/413 |
| 6,053,917 A | 4/2000 | Sherman et al. | |
| 6,080,155 A | 6/2000 | Michelson | |
| 6,083,227 A | 7/2000 | Saurat | |
| 6,129,730 A | 10/2000 | Bono et al. | |
| 6,132,434 A | 10/2000 | Sherman et al. | |
| 6,139,550 A | 10/2000 | Michelson | |
| 6,159,214 A | 12/2000 | Michelson | |
| 6,166,666 A | 12/2000 | Kadyk | |
| 6,168,597 B1 | 1/2001 | Biedermann et al. | |
| 6,193,721 B1 | 2/2001 | Michelson | |
| 6,210,412 B1 | 4/2001 | Michelson | |
| 6,224,602 B1 | 5/2001 | Hayes | |
| 6,270,498 B1 | 8/2001 | Michelson | |
| 6,280,442 B1 | 8/2001 | Barker et al. | |
| 6,287,311 B1 | 9/2001 | Sherman et al. | |
| 6,293,949 B1 | 9/2001 | Justis | |
| D449,692 S | 10/2001 | Michelson | |
| 6,309,391 B1 | 10/2001 | Crandall et al. | |
| 6,312,431 B1 | 11/2001 | Asfora | |
| 6,364,880 B1 | 4/2002 | Michelson | |
| 6,368,321 B1 | 4/2002 | Jackson | |
| 6,383,186 B1 | 5/2002 | Michelson | |
| 6,398,783 B1 | 6/2002 | Michelson | |
| 6,413,259 B1 | 7/2002 | Lyons et al. | |
| 6,416,528 B1 | 7/2002 | Michelson | |
| 6,428,542 B1 | 8/2002 | Michelson | |
| 6,440,132 B1 | 8/2002 | Jackson | |
| 6,440,139 B2 | 8/2002 | Michelson | |
| 6,454,770 B1 * | 9/2002 | Klaue | 606/281 |
| 6,454,771 B1 | 9/2002 | Michelson | |
| 6,454,773 B1 | 9/2002 | Sherman et al. | |
| 6,458,133 B1 * | 10/2002 | Lin | 606/279 |
| 6,458,158 B1 | 10/2002 | Anderson et al. | |
| 6,471,705 B1 | 10/2002 | Biedermann et al. | |
| 6,503,252 B2 * | 1/2003 | Hansson | 606/65 |
| 6,508,820 B2 * | 1/2003 | Bales | 606/62 |
| 6,527,776 B1 | 3/2003 | Michelson | |
| 6,533,786 B1 | 3/2003 | Needham | |
| 6,540,748 B2 | 4/2003 | Lombardo | |
| 6,585,740 B2 * | 7/2003 | Schlapfer et al. | 606/308 |
| 6,589,245 B1 * | 7/2003 | Weiler et al. | 623/13.14 |
| 6,592,586 B1 | 7/2003 | Michelson | |
| 6,616,666 B1 | 9/2003 | Michelson | |
| 6,620,163 B1 | 9/2003 | Michelson | |
| 6,635,059 B2 * | 10/2003 | Randall et al. | 606/916 |
| 6,652,525 B1 | 11/2003 | Assaker | |
| 6,656,184 B1 | 12/2003 | White et al. | |
| 6,660,004 B2 | 12/2003 | Barker et al. | |
| 6,663,635 B2 | 12/2003 | Frigg et al. | |
| 6,712,818 B1 | 3/2004 | Michelson | |
| 6,723,100 B2 | 4/2004 | Biedermann et al. | |
| 6,736,820 B2 | 5/2004 | Biedermann et al. | |
| 6,755,835 B2 | 6/2004 | Schultheiss et al. | |
| 6,766,781 B2 | 7/2004 | Penzel | |
| 6,793,658 B2 | 9/2004 | LeHuec et al. | |
| D499,692 S | 12/2004 | Brown | |
| 6,887,242 B2 | 5/2005 | Doubler et al. | |
| 6,916,320 B2 | 7/2005 | Michelson | |
| 6,926,718 B1 | 8/2005 | Michelson | |
| 6,936,050 B2 | 8/2005 | Michelson | |
| 6,936,051 B2 | 8/2005 | Michelson | |
| 6,949,100 B1 | 9/2005 | Venturini | |
| 6,969,390 B2 | 11/2005 | Michelson | |
| 7,001,387 B2 * | 2/2006 | Farris et al. | 606/287 |
| 7,041,105 B2 | 5/2006 | Michelson | |
| 7,044,952 B2 | 5/2006 | Michelson | |
| 7,044,953 B2 | 5/2006 | Capanni | |
| 7,063,701 B2 | 6/2006 | Michelson | |
| 7,063,702 B2 | 6/2006 | Michelson | |
| 7,074,221 B2 | 7/2006 | Michelson | |
| 7,077,844 B2 | 7/2006 | Michelson | |
| 7,094,239 B1 | 8/2006 | Michelson | |
| 7,097,645 B2 | 8/2006 | Michelson | |
| 7,112,202 B2 | 9/2006 | Michelson | |
| 7,112,222 B2 * | 9/2006 | Fraser et al. | 623/17.11 |
| 7,118,573 B2 | 10/2006 | Michelson | |
| 7,137,984 B2 | 11/2006 | Michelson | |
| 7,175,624 B2 | 2/2007 | Konieczynski et al. | |
| 7,186,255 B2 | 3/2007 | Baynham et al. | |
| 7,186,256 B2 * | 3/2007 | Michelson | 606/71 |
| 7,195,633 B2 * | 3/2007 | Medoff et al. | 606/309 |
| 7,207,994 B2 | 4/2007 | Vlahos | |
| 7,273,481 B2 | 9/2007 | Lombardo et al. | |
| 7,306,605 B2 | 12/2007 | Ross | |
| 8,162,998 B2 * | 4/2012 | Schlienger et al. | 606/315 |
| 2002/0016594 A1 * | 2/2002 | Schlapfer et al. | 606/73 |
| 2002/0169453 A1 | 11/2002 | Berger | |
| 2002/0183754 A1 | 12/2002 | Michelson | |
| 2003/0018335 A1 | 1/2003 | Michelson | |
| 2003/0045880 A1 | 3/2003 | Michelson | |
| 2004/0006345 A1 * | 1/2004 | Vlahos et al. | 606/73 |
| 2004/0044345 A1 * | 3/2004 | DeMoss et al. | 606/73 |
| 2004/0122431 A1 | 6/2004 | Biedermann et al. | |
| 2004/0181229 A1 | 9/2004 | Michelson | |
| 2004/0215195 A1 * | 10/2004 | Shipp et al. | 606/69 |
| 2004/0220571 A1 * | 11/2004 | Assaker et al. | 606/69 |
| 2004/0236334 A1 | 11/2004 | Michelson | |
| 2004/0236533 A1 | 11/2004 | Michelson | |
| 2004/0239127 A1 | 12/2004 | Lodwick, Jr. | |
| 2004/0243129 A1 * | 12/2004 | Moumene et al. | 606/73 |
| 2005/0021036 A1 * | 1/2005 | Whitmore et al. | 606/73 |
| 2005/0027297 A1 | 2/2005 | Michelson | |
| 2005/0027298 A1 | 2/2005 | Michelson | |
| 2005/0033300 A1 | 2/2005 | Frenk et al. | |
| 2005/0033433 A1 * | 2/2005 | Michelson | 623/17.11 |
| 2005/0038436 A1 | 2/2005 | Michelson | |
| 2005/0038438 A1 * | 2/2005 | Anderson et al. | 606/73 |
| 2005/0059971 A1 | 3/2005 | Michelson | |
| 2005/0101961 A1 | 5/2005 | Huebner et al. | |
| 2005/0137598 A1 | 6/2005 | Auth | |
| 2005/0187552 A1 | 8/2005 | Michelson | |
| 2005/0192578 A1 * | 9/2005 | Horst | 606/69 |
| 2005/0228388 A1 * | 10/2005 | Brodke et al. | 606/73 |
| 2005/0273101 A1 | 12/2005 | Schumacher | |
| 2006/0095040 A1 | 5/2006 | Schlienger et al. | |
| 2006/0106383 A1 | 5/2006 | Biedermann et al. | |
| 2006/0106389 A1 * | 5/2006 | Reber et al. | 606/72 |
| 2006/0116686 A1 | 6/2006 | Crozet | |
| 2006/0122612 A1 * | 6/2006 | Justin et al. | 606/73 |
| 2006/0135960 A1 | 6/2006 | Munro et al. | |
| 2006/0142770 A1 | 6/2006 | Capanni | |
| 2006/0149263 A1 * | 7/2006 | Newcomb et al. | 606/73 |
| 2006/0149265 A1 * | 7/2006 | James et al. | 606/73 |
| 2006/0173462 A1 | 8/2006 | Kay | |
| 2006/0195099 A1 | 8/2006 | Bottlang | |
| 2006/0200150 A1 | 9/2006 | Homaki et al. | |
| 2006/0217727 A1 | 9/2006 | Munro et al. | |
| 2006/0276791 A1 * | 12/2006 | Shluzas | 606/61 |
| 2007/0043372 A1 | 2/2007 | Willmann | |
| 2007/0053765 A1 * | 3/2007 | Warnick et al. | 411/378 |
| 2007/0083206 A1 | 4/2007 | Du | |
| 2008/0015595 A1 * | 1/2008 | Renard et al. | 606/73 |
| 2008/0038088 A1 * | 2/2008 | Matthiesen et al. | 411/411 |
| 2008/0249579 A1 * | 10/2008 | Taylor | 606/317 |
| 2011/0106157 A1 * | 5/2011 | Melkent et al. | 606/246 |
| 2011/0137355 A1 * | 6/2011 | Rinner | 606/315 |

\* cited by examiner

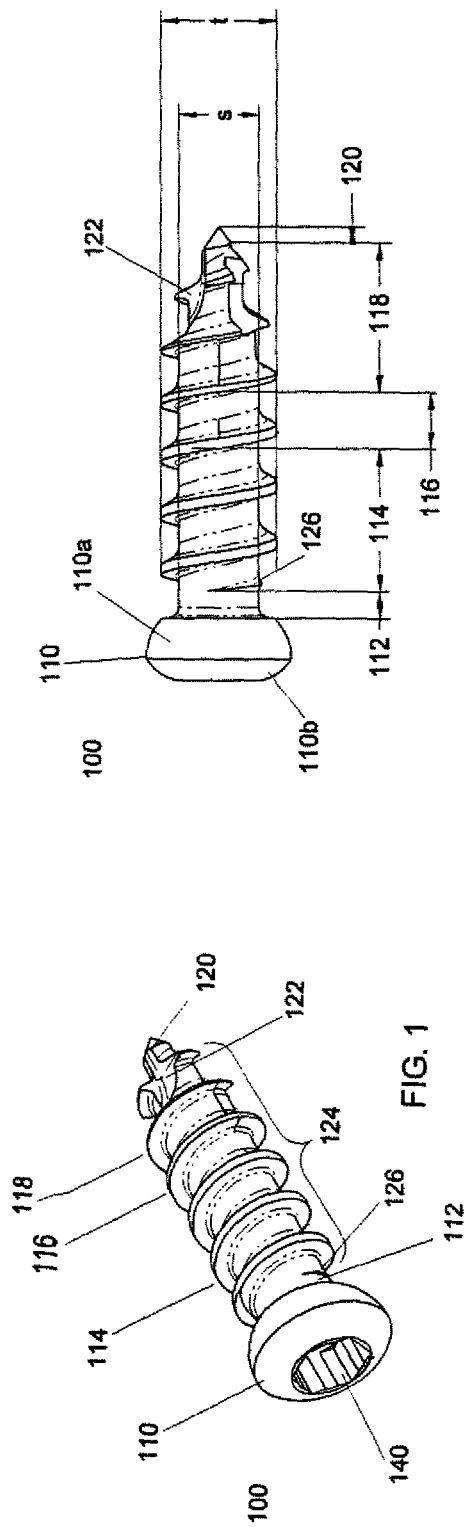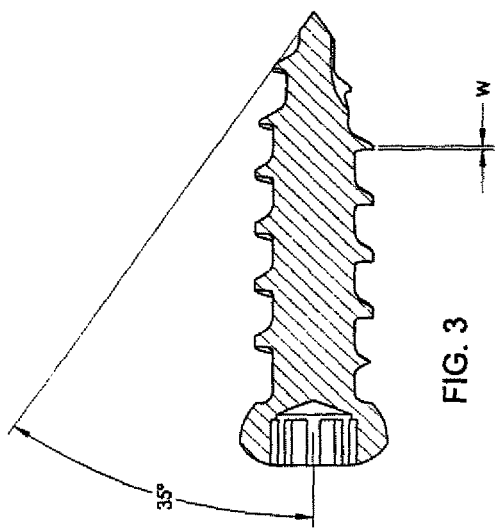

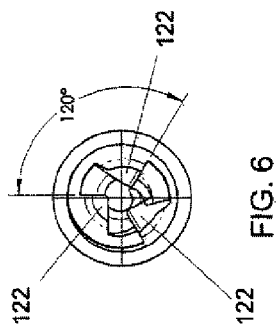
FIG. 6
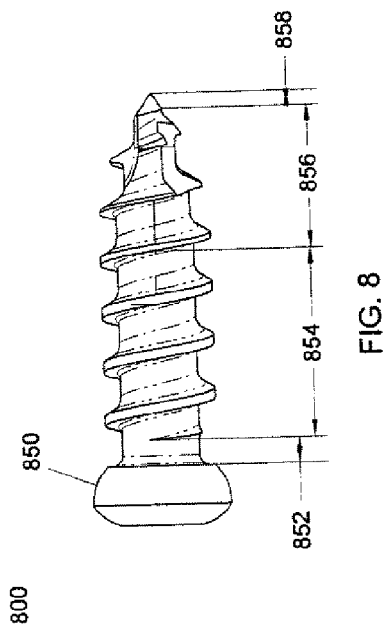
FIG. 8
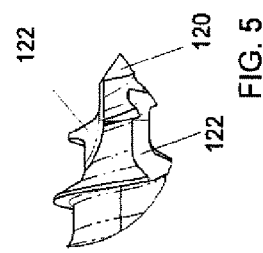
FIG. 5
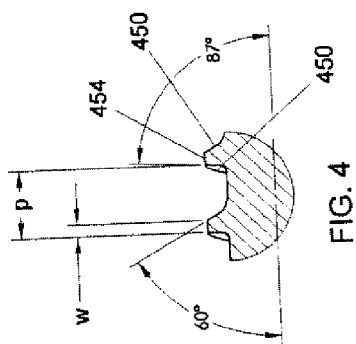
FIG. 4
FIG. 7

BONE SCREW

FIELD OF THE INVENTION

The present invention relates generally to devices and methods for the stabilization of bone structures, and more particularly to bone screws and medical devices used to stabilize bone structures.

BACKGROUND OF THE INVENTION

Bone screws are used for a multitude of purposes, including attaching various medical devices to bone. One such application involves the use of bone screws to attach a plate to adjacent bone structures or fragments to promote fusion of the structures or fragments into a unitary structure.

As an example, bone screws can be used to attach an anterior cervical plate to the relevant portion of a patient's anterior cervical spine to achieve fusion. Anterior cervical spinal fusion is a common approach for the surgical management of cervical disk disease, in which two or more vertebrae are brought together under conditions whereby the vertebrae fuse together to form a unitary member of the spinal column. Frequently, if there is significant spinal cord compression or if there is more than one disk level involved, a small plate is affixed on the anterior surface of the cervical vertebrae to provide greater permanent stability. In carrying out the procedure, the members must be brought together under conditions that are critically controlled to prevent infection, maintain alignment of opposing members, and allow for the stress in the bone that is generated as the healing process matures. According to the present art, the plates commonly used for cervical spinal fusion are fabricated from titanium with holes through which screws are inserted to secure the plate to neighboring vertebrae.

An additional application of bone screws in the spinal field is in the stabilization of the lumber spine. In one typical procedure, a bendable rod is attached by bone screws to various vertebrae along a portion of the patient's spine. Such a rod may have apparatus, including holes, configured to receive bone screws to secure the rod to the patient's vertebrae.

As another example, bone screws can be used to attach sternal closure plates to a patient's sternum following a median sternotomy. Many surgical procedures require a median sternotomy, a procedure in which an incision is made along the sternum such that it can be separated laterally into two sides, to allow access to the tissues and organs located in a patient's thoracic cavity. Following the surgical procedure, the two sides of the sternum must be secured together, which may be accomplished by attaching a plating system to them. The plating systems used for sternal closure may have holes through which bone screws are inserted to secure the plating system to the two sides of the sternum.

It has been recognized that osseous trans-differentiation during the course of bone healing may have a significant role in improving the structural integrity of healed bone following surgery or trauma. This process of bone remodeling may, however, result in partial extrusion of the bone screws placed during surgery to fix the position of bones or fragments if the fusion does not take place. Post-operative screw extrusion can be dangerous and may require further surgery. Locking the screws into place to disallow any degree of post-operative movement has been found to be undesirable because it precludes trans-differentiation, but it can be important that the movement of the screws be somewhat restricted to prevent more than slight screw extrusion.

The design of the bone screw is important, as it affects the speed and ease of implantation during surgery, the stability of fastening following surgery, and the potential for screw extrusion, among other characteristics. For example, some prior art screw designs require a drilling operation and/or a tapping operation to prepare the bone for the screw prior to its insertion. Such operations have numerous disadvantages, including the danger associated with introducing an additional instrument into the spinal canal during surgery, the potential for fracture formation, and the removal of bone material. Further, shearing of the thread crests during insertion has been experienced with some prior art screw designs, leading to the release of tiny metal shards in the patient. Further, some prior art screw designs have caused problems with loosening, breaking, and extruding from the bone. Again, this can create a dangerous condition that requires further surgery. Therefore, it is desirable to have a new and improved bone screw.

In addition to the design of the bone screw alone, the design of the bone screw in relation to a corresponding medical device, such as an anterior cervical plate or sternal closure plate, can affect the potential for screw extrusion. It is desirable to have a corresponding bone screw and plate system that allows only a beneficial degree of post-operative screw extrusion.

SUMMARY OF THE INVENTION

An improved bone screw is provided for securing a medical device to bone. In one embodiment, the bone screw includes a screw head, a shaft with multiple regions therein, and a sharp tip. The shaft regions include a smooth cylindrical shaft region, a first cylindrical shaft region with external threading having a first pitch and first crest width, a second cylindrical shaft region with external threading having a transitional pitch and crest width, and a tapered shaft region with external threading having a second smaller pitch and second smaller crest width and further having at least one recessed flute. Each of the shaft regions is optional in a particular embodiment of the bone screw.

In one embodiment, the head includes a recessed portion for receiving a tool. In one embodiment, the tip has no threading or fluting.

The external threading comprises a forward face and a backward face. In one embodiment, the angle between the forward face and the central axis of the screw is substantially constant throughout the threading. In one embodiment, the angle between the backward face and the central axis of the screw is substantially constant throughout the threading. In a further embodiment, both angles are substantially constant throughout the threading.

In one embodiment, the shaft diameter is substantially equal in the smooth cylindrical shaft region and the first and second threaded cylindrical shaft regions. In one embodiment, the diameter of the threading is substantially constant along a majority of its length. In one embodiment, there is a ramping region between the smooth cylindrical shaft region and the first cylindrical shaft region. The ramping region has external threading that progressively increases in depth.

In one embodiment, the tapered shaft region includes three recessed flutes. In a particular embodiment, each of the three flutes spans an angle of about 90 degrees.

In one aspect, a bone screw is provided for engaging with a bone screw hole in an anterior cervical plate. In one embodiment, the bone screw includes a sharp tip, a shaft with multiple regions therein, and a head. The shaft regions include a tapered shaft region with external threading, having a threading diameter smaller than the diameter of the screw hole along at least a portion of this region; a first cylindrical shaft region with external threading, at least a portion of which is sized and shaped to engage with the screw hole; and a second cylindrical shaft region without external threading. Each of the shaft regions is optional in a particular embodiment. The diameter of the shaft in all shaft regions is smaller than the diameter of the screw hole.

In one embodiment, the head includes a recessed portion for receiving a tool. In one embodiment, the tip has no threading or fluting.

The external threading comprises a forward face and a backward face. In one embodiment, the angle between the forward face and the central axis of the screw is substantially constant throughout the threading. In one embodiment, the angle between the backward face and the central axis of the screw is substantially constant throughout the threading. In a further embodiment, both angles are substantially constant throughout the threading. In one embodiment, the diameter of the threading is substantially constant along said first cylindrical shaft region. In one embodiment, the diameter of the shaft is substantially equal in the first cylindrical shaft region and second cylindrical shaft region.

In one embodiment, there is a ramping region between said first cylindrical shaft region and said second cylindrical shaft region. The ramping region has external threading that progressively increases in depth.

In one embodiment, the tapered shaft region includes at least one recessed flute. In a further embodiment, the tapered shaft region includes three recessed flutes. In a particular embodiment, each of the three flutes spans an angle of about 90 degrees.

In another aspect, an anterior cervical plating system is provided. The plating system includes an anterior cervical plate with at least one bone screw hole, and a bone screw. The bone screw includes a head, a body, and a tip. The body has a region adjacent to the head that is unthreaded, and the rest of the body has external threading. The diameter of the head is larger than the diameter of the bone screw hole. The diameter of the body is smaller than the bone screw hole. At least a portion of the threading has a diameter that is larger than the diameter of the bone screw hole, and that portion engages with the bone screw hole when the screw is rotated through the hole. When the screw is fully inserted in the hole, the unthreaded portion of the screw is positioned within the hole.

DESCRIPTION OF THE DRAWINGS

The objects and advantages of the present invention will be better understood and more readily apparent when considered in conjunction with the following detailed description and accompanying drawings which illustrate, by way of example, preferred embodiments of the bone screw and in which:

FIG. 1 is a perspective view of one embodiment of the bone screw.

FIG. 2 is a side view of one embodiment of the bone screw.

FIG. 3 is a cross-sectional view of one embodiment of the bone screw.

FIG. 4 is a cross-sectional view of one embodiment of the external threading on the bone screw.

FIG. 5 is a side view of the front portion of one embodiment of the bone screw.

FIG. 6 is a plan view of one embodiment of the front end of the bone screw.

FIG. 7 is a plan view of one embodiment of the head of the bone screw.

FIG. 8 is a side view of one embodiment of the bone screw, designed to engage with a medical plate.

DETAILED DESCRIPTION OF THE PREFERRED EMBODIMENTS

Figure 10:
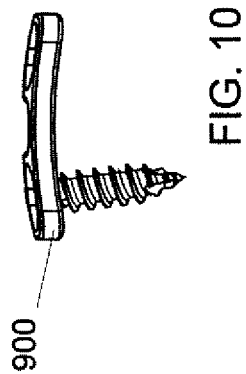
FIG. 10 is a side view of one embodiment of the bone screw inserted through a screw hole in an anterior cervical plate.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The bone screw can be further understood with reference to the exemplary, non-limiting embodiments illustrated in FIGS. 1-10.

The "front" of the screw will be used herein to refer to the end with the tip, and the "back" of the screw will be used herein to refer to the end with the head.

One embodiment of the bone screw is shown in perspective view in FIG. 1. The bone screw 100 includes a head 110 with a recessed portion 140, an unthreaded region 112 adjacent the head 110, a body 124 with external threading, and a tip 120. There are multiple regions 114, 116, 118 shown within the threaded body 124. The region adjacent the tip 120 includes multiple flutes 122. FIG. 2 shows a side view of the bone screw embodiment of FIG. 1, and FIG. 3 shows a cross-sectional view of the bone screw embodiment of FIG. 1.

Figure 9:
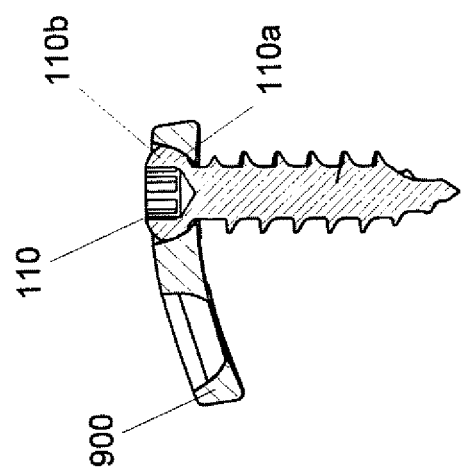
FIG. 9 is a cross-sectional embodiment of one embodiment of the bone screw inserted through a screw hole in an anterior cervical plate.

The head 110 may be any shape, such as round, oval, pentagonal, and hexagonal. In one embodiment, as shown in FIG. 1, the head 110 is round. The design and dimensions of the head 110 can vary, but the head is larger than the bone screw hole so as to prevent passage therethrough. For certain applications, such as use with an anterior cervical plating system or a sternal closure plating system, the head 110 preferably has a low profile and smooth edges, to reduce irritation in the patient's body upon implantation. In the embodiment shown in FIG. 2, the edges of the head 110 are smooth and rounded. Further, the head may be sized and shaped to correspond to the area surrounding a bone screw hole in a medical device, such as a plating system. As shown in FIG. 2, the head 110 may have two rounded portions 110a, 110b, shown to be separated by a line. One or both of the rounded portions 110a, 110b of the head 110 may be designed to fit within the indentation surrounding a bone screw hole on a plate device. The front rounded portion 110a can be sized and shaped to fit within the indentation surrounding the bone screw hole. In one embodiment, the entire back rounded portion 110b has a profile above the top plane of the plate device 900, and in another embodiment, only the very top of the back rounded portion 110b has a profile above the plate of the plate device 900, as shown in FIG. 9. Alternatively, the head 110 can be sized and shaped such that the entire head 110 is level with or below the plane of the top surface of a plate device 900, as shown in FIG. 10.

For other applications, such as with a lumbar spinal rod, the screw may have an approximately spherical head, or polyaxial head, as known in the pedicle screw field.

The head may have a recessed portion for receiving a rotatable tool, such as a drill or screwdriver. The shape, depth, and other dimensions of the recessed portion may vary to correspond with a given rotatable tool. In one embodiment, as shown in FIG. 1, the recessed portion 140 is hexagonal. FIG. 7 shows the top of another embodiment of the screw head 710. The embodiment of FIG. 7 has a recessed portion 740 that is round. The recessed portion 740 shown in FIG. 7 is centered on the screw head 710, but it could be offset. Also, the size of the recessed portion 710 relative to the head 710 may vary. Further, the head may have a plurality of recessed portions.

Shown adjacent to the head 110 in FIG. 1 is an unthreaded portion 112. The length of the unthreaded portion 112 may vary. In one embodiment, the length of the unthreaded portion 112 is between 0.5 mm and 3 mm. In a particular embodiment, the length is 1.5 mm. Depending on the application for which the screw is being used, the unthreaded region can be rounded or cylindrical. For certain applications, the screw may not contain an unthreaded region. If cylindrical, the unthreaded region has a substantially constant diameter. The diameter of the unthreaded portion 112 may vary, but is smaller than the diameter of the head 110. In one embodiment, the diameter of the unthreaded portion 112 is substantially equal to the shaft diameter of the first cylindrical shaft region 114. External threading begins to the front of the unthreaded region 112. The screw 100 may be designed to engage with the bone screw hole of a medical device. For example, advantageously a portion of the external threading may engage with a hole when the screw 100 is rotated through the hole, and the screw 100 may disengage with the hole upon full insertion, when the unthreaded portion 112 is positioned in the bone screw hole.

FIG. 4 provides a close-up view of one embodiment of external threading. The threading is formed by a forward face 450, defined as the face pointed toward the front, or tip, of the screw, a backward face 452, defined as the face pointed toward the back, or head, of the screw, and a crest 454 joining the forward face 450 and backward face 452. The forward face 450 and backward face 452 each form an angle with the central axis of the screw. The central axis extends from the tip through the center of the screw, as shown by a horizontal line in FIG. 3. The central axis is also represented by a horizontal line in FIG. 4. The angle between the forward face 450 and central axis may vary along the length of the screw. Similarly, the angle between the backward face 452 and central axis may vary along the length of the screw. The threading has a pitch, defined as the distance between corresponding points on subsequent thread revolutions, shown in FIG. 4 as p. The threading has a crest width, defined as the width of the crest, shown in FIGS. 3 and 4 as w. The pitch and crest width may vary along the length of the screw.

In one embodiment, the pitch and crest width vary in multiple regions within the threaded portion of the body 124, as shown in FIG. 1. FIGS. 1 and 2 show three regions: a first threaded region 114, a second threaded transitional region 116, and a third threaded region 118.

One sub-region of the body 124 is a first threaded region 114 with external threading having a first pitch and a first crest width. The first threaded region 114 may comprise any number of revolutions. The number of revolutions in the first threaded region 114 does not have to be an integer; that is, the region could end with an incomplete revolution. In one embodiment, the first threaded region 114 comprises between about 1 and about 6 revolutions of thread. In a particular embodiment, the first threaded region 114 comprises about 3 revolutions. The pitch of the thread remains substantially constant throughout the first threaded region 114. The pitch in the first threaded region 114 is larger than the pitch in the third threaded region 118. In one embodiment, the pitch in the first threaded region 114 is between 3 mm and 9 mm, and in one particular embodiment it is about 6 mm.

The crest width of the threading also remains substantially constant throughout the first threaded region 114, and is larger than the crest width in the third threaded region 118. In one embodiment, the crest width in the first threaded region 114 is between 0.3 mm and 0.5 mm. Advantageously, a crest width of this relatively large size resists shearing upon contact with a screw hole, such as in a spinal stabilization plate.

The first threaded region 114 has a shaft diameter, shown in FIG. 2 as s, and a threading diameter, shown in FIG. 2 as t. The shaft diameter and threading diameter are shown to be substantially constant throughout the length of the first threaded region 114. When the shaft diameter is substantially constant, the shaft in the first threaded region 114 is cylindrical. The diameter of the shaft can vary greatly, for example, from 1.5 mm to 8 mm, depending on the application for which the screw is being used. The diameter of the threading can also vary greatly. In one embodiment, the shaft diameter of the first threaded region is between 2.5 mm and 3.5 mm, and in a particular embodiment the shaft diameter is about 2.9 mm. In one embodiment, the threading diameter of the first threaded region 114 is between 3 mm and 5 mm, and in a particular embodiment the threading diameter is 4 mm. In another embodiment, the shaft diameter is larger, such as between 4 mm and 8 mm, and the threading diameter is between 7 mm and 10 mm.

The angle between the forward face 450 and the central axis, shown close-up in FIG. 4, may vary in the first threaded region 114. This angle is between 40 degrees and 80 degrees, preferably between 50 and 70 degrees, and more preferably about 60 degrees. In one embodiment, the forward angle remains substantially constant throughout the first threaded region 114 at about 60 degrees. The angle between the backward face 452 and the central axis, shown close-up in FIG. 4, also may vary in the first threaded region 114. This backward angle is between 60 degrees and 120 degrees, preferably between 80 and 100 degrees, and more preferably about 87 to 90 degrees. In one embodiment, the backward angle remains substantially constant throughout the first threaded region 114 at about 87 degrees.

The first threaded region 114 may comprise a portion in which the depth of the threading, measured from the outer surface of the shaft to the crest, progressively increases. After the unthreaded region 112, the threading may ramp out of the screw shaft and increase in depth. After the initial ramping, the threading diameter of the first threaded region 114 may be substantially constant.

Alternatively, there may be a separate ramping region 126 between the unthreaded region 112 and the first threaded region 114, in which the depth of the threading progressively increases and the pitch and crest width may differ from the pitch and crest width in the first threaded region 114. A ramping region 126 is shown in part in FIGS. 1 and 2. In one embodiment, the pitch in the ramping region 126 is smaller than or substantially equal to the pitch in the first threaded region 114. In one embodiment, the crest width in the ramping region 126 is smaller than the crest width in the first threaded region 114. The ramping region 126 may comprise any number of revolutions. The number of revolutions in the ramping region 126 does not have to be an integer; that is, the region could end with an incomplete revolution. In one embodiment, the ramping region 126 comprises less than 1 thread revolution, as shown in FIG. 2. The ramping region 126 is shown in FIG. 2 starting near the central axis of the screw and proceeding toward the bottom of the figure, and the ramping region 126 continues around the shaft outside of the view of the figure. At the point the threading comes back into view at the top of FIG. 2, the first threaded region 114 has begun.

The region shown in FIG. 1 adjacent to the first threaded region 114, moving in the direction away from the head 110, is a second threaded transitional region 116 with external threading that transitions from the pitch of the first threaded region 114 to the pitch of the third threaded region 118, and from the crest width of the first threaded region 114 to the crest width of the third threaded region 118. Thus, the pitch and/or crest width preferably decrease within the transitional region 116.

The transitional region 116 may comprise any number of thread revolutions. The number of thread revolutions in the transitional region 116 does not have to be an integer; that is, the region could end with an incomplete revolution. In one embodiment, the transitional region 116 comprises between less than 1 revolution and about 3 revolutions of the thread. In a particular embodiment, the transitional region 116 comprises about 1 revolution. The transitional region 116 has a shaft diameter, shown in FIG. 2 as s, and a threading diameter, shown in FIG. 2 as t. The shaft diameter and threading diameter are shown to be substantially constant throughout the length of the transitional region 116 and are shown to be substantially equal to the shaft diameter and threading diameter of the first threaded region 114. The shaft diameter and threading diameter of the transitional region 116 can vary as described for the first threaded region 114.

The angle between the forward face 450 and the central axis, shown close-up in FIG. 4, may vary in the transitional region 116. This angle is between 40 degrees and 80 degrees, preferably between 50 and 70 degrees, and more preferably about 60 degrees. In one embodiment, the forward angle remains substantially constant throughout the transitional region 116 at about 60 degrees. The angle between the backward face 452 and the central axis, shown close-up in FIG. 4, also may vary in the transitional region 116. This backward angle is between 60 degrees and 120 degrees, preferably between 80 and 100 degrees, and more preferably about 87 to 90 degrees. In one embodiment, the backward angle remains substantially constant throughout the transitional region 116 at about 87 degrees.

The region shown in FIG. 1 adjacent to the transitional region 116, moving in the direction away from the head 110, is a third threaded region 118 having a tapering shaft diameter and having threading and at least one recessed flute 122. The threading and fluting extend over at least a portion of the third threaded region 118. FIG. 5 provides a close-up view of part of the third threaded region 118 shown in FIG. 2. Moving back from the tip 122 itself, there may be a portion having fluting but no threading. There also may be a portion having both fluting and threading, or a portion having only threading. The distance from the tip 120 to the start of the fluting and/or threading may vary. Because of the flute(s) 122, there may be cut-outs in the threading, making it discontinuous in the third threaded region 118. The number of flutes 122 may vary. The angle spanned by each flute 122 may also vary.

In a particular embodiment, there are 3 flutes 122, each spanning about a 90 degree angle, as shown in FIG. 6. An angle of about 90 degrees is advantageous because it provides sufficient area for collecting bone material and removing it from the path of the subsequent regions of the screw as they are inserted into the bone. The flutes 122 may be offset from the point of the tip 120, shown as a cross in FIG. 6. The flutes 122 may be offset by different amounts, and the orientation of the flutes 122 with respect to the point and to each other may vary. FIG. 6 shows the angle between a cutting edge of one flute 122 the corresponding cutting edge of another flute 122 to be 120 degrees. The third threaded region 118 may comprise any number of thread revolutions. The number of revolutions in the third threaded region 118 does not have to be an integer; that is, the region could end with an incomplete revolution. In one embodiment, the third threaded region 118 comprises between about 1 and about 6 revolutions of thread. In a particular embodiment, the third threaded region 118 comprises about 4 revolutions (counting the cut-out areas as part of a revolution).

Despite that the threading may not be continuous, the pitch of the threading that is present in the third threaded region 118 remains substantially constant. The pitch in the third threaded region 118 is smaller than the pitch in the first threaded region 114. In one embodiment, the pitch in the third threaded region 118 is between 1 mm and 5 mm, and in one particular embodiment is about 3 mm. The crest width of the threading also remains substantially constant throughout the third threaded region 118, and is smaller than the crest width in the first threaded region 114. In one embodiment, the crest width in the third threaded region 118 is between 0.05 mm and 0.2 mm. The small crest width may be advantageous because it allows the threading to have sharp crests that bite into the bone during insertion of the screw 100. In one embodiment, the crest width is about 0.13 mm. For certain applications, such as those requiring a larger screw, a larger crest width may be desired. The diameter of the shaft, measured from its outer surface to the central axis, may taper over the entire third threaded region 118 or a portion of the third threaded region 118. The tapering occurs in the direction toward the tip 120. FIGS. 2 and 3 shows that the threading diameter, measured from the crest to the central axis, may decrease as the shaft diameter decreases. The starting shaft diameter and threading diameter can vary as described for the first threaded region.

The angle between the forward face 450 and the central axis, shown close-up in FIG. 4, may vary in the third threaded region 118. This angle is between 40 degrees and 80 degrees, preferably between 50 and 70 degrees, and more preferably about 60 degrees. In one embodiment, the forward angle remains substantially constant throughout the third threaded region 118 at about 60 degrees. The angle between the backward face 452 and the central axis, shown close-up in FIG. 4, also may vary in the third threaded region 118. This backward angle is between 60 degrees and 120 degrees, preferably between 80 and 100 degrees, and more preferably about 87 to 90 degrees. In one embodiment, the backward angle remains substantially constant throughout the third threaded region 118 at about 87 degrees.

In one embodiment, both the forward angle and the backward angle remain substantially constant throughout all threading along the body 124 of the screw. These angles should be chosen to contribute to the screw having maximal bite in the bone and gaining sufficient purchase for secure placement in the bone. In a particular embodiment, the forward angle remains about 60 degrees and the backward angle remains about 87 degrees throughout the threading.

At the front end of the screw is a tip 120. The tip 120 has a sharp point and can be without threading or fluting. Advantageously, the sharp tip 122 acts similar to an awl and eliminates the need for the target area on the bone to be pre-drilled in preparation for the screw's insertion. The length of the tip 122 may vary. In one embodiment, the length of the tip 122 is less than 1 mm. For certain applications, such as those requiring a larger screw, a longer tip may be desired. The side angle of the tip 120, defined as the angle between the central axis and one side of the tip 120, may vary. In one embodiment, the side angle is about 35 degrees, as shown in FIG. 3.

The bone screw may be made of any biocompatible material. In one embodiment, the bone screw is made of titanium alloy. The bone screw may be employed with any type of medical device.

The features of the bone screw may have several functional advantages, some of which are discussed above. Additional advantages may be gained by the combination of the bone screw with a bone screw hole in a medical device, for example an anterior cervical plate or sternal closure plate.

A portion of the external threading on the screw can engage with a screw hole on a plate or other medical device. One embodiment of a bone screw designed for combination with an anterior cervical plate is shown in FIG. 8. The bone screw 800 includes a tip 858, a tapered shaft region 856 having external threading, a first cylindrical shaft region 854 having external threading, a second cylindrical shaft region 852 without external threading, and a head 850. The diameter of the head 850 is larger than the diameter of the screw hole. The shaft diameters of the tapered shaft region 856 and first and second cylindrical regions 854, 852 are smaller than the diameter of the hole. The diameter of the first and second cylindrical regions 854, 852 may be substantially equal. The tip 858 may be without threading and fluting. In one embodiment, the tapered shaft region 856 has at least one recessed flute. In a particular embodiment, it has three recessed flutes, each spanning an angle of about 90 degrees. The tip 858 and at least a portion of the tapered shaft region 856, including the external threading thereon, are sized and shaped to fit through the screw hole without contacting the edges of the hole. This is beneficial for implantation, as it allows part of the front end of the screw 800 to be inserted through the screw hole, while the plate is pressed against the target bone, and for the screw 800 to be drilled partially into the bone before the threading engages the screw hole.

Once the diameter of the external threading exceeds the diameter of the screw hole, which can occur in the tapered shaft region 856 or in the first cylindrical shaft region 854 of the screw 800, the screw 800 cannot pass further through the hole without the threading engaging with the edges of the hole. In one embodiment, the threading diameter is substantially constant in the first cylindrical shaft region 854. As described above, and shown close-up in FIG. 4, the threading is formed by a forward face 450, a backward face 452, and a crest 452, and the forward face 450 and backward face 452 each form an angle with the central axis of the screw. These angles should be chosen such that, upon rotation, the threading engages with the edges of the hole. The forward and backward angles may vary within the tapered shaft region 856 and first cylindrical shaft region 854 or may remain substantially constant within these regions or throughout both regions. The pitch and crest width of the threading may vary within or between the tapered shaft region 856 and first cylindrical shaft region 854. In one embodiment, the pitch and crest width increase toward the back of the screw. It can be advantageous to have a smaller crest width on the tapered shaft region 856 to provide sharp crests that can bite into the bone during insertion.

With further rotation, the threading continues to engage with the hole throughout the first cylindrical shaft region 854, and the rest of the screw 800, except for the head 850, may pass through the hole. At the point the unthreaded second cylindrical shaft region 852 reaches the hole, there is no threading engaged with the hole, meaning the screw 800 is disengaged from the hole. Thus, when fully inserted such that only the head 850 remains above the plane of the hole, the screw 800 is disengaged from the hole. The dimensional relationship of the unthreaded region 852 to the hole may vary, but in one embodiment, the unthreaded region 852 has a diameter small enough to avoid a tight fit in the hole. The length of the unthreaded region 852 also may vary, but preferably the length of the unthreaded region 852 is greater than the depth of the screw hole edges. That is, the screw can be inserted such that only the unthreaded region 852 extends through the screw hole, with the screw head 850 and threading to the top and bottom, respectively, of the hole.

The transition from the threaded first cylindrical shaft region 854 to the unthreaded second cylindrical shaft region 852 may be advantageous in multiple respects. Given the disengagement of the screw 800 from the plate when the unthreaded region 852 passes through the hole, the screw 800 is not locked in place with respect to the plate. This may allow some movement of the screw 800 with respect to the plate, as can be caused by trans-differentiation during the bone healing process. Further, the unthreaded region 852 may be of a sufficient length to cause disengagement when the screw 800 is inserted with up to 15 degrees of variance from an angle perpendicular to the plane of the hole. This allows for beneficial engagement to occur given a range of normal variability in the insertion of a bone screw. Further, when the screw is fully inserted such that the unthreaded region 852 extends through the hole, as shown for one embodiment in FIG. 9, the threading of the first cylindrical shaft region 854 is beneath the edges of the hole and resists extrusion of the screw 800 from the bone. The length of the unthreaded region 852 may affect the amount of extrusion allowed before the threading contacts the edges of the hole, and the length may be chosen with consideration of the desired amount of extrusion.

Between the threaded first cylindrical shaft region 854 and the unthreaded second cylindrical shaft region 852, there may be a ramping region with external threading that increases in depth, the depth being measured from the outer surface of the shaft to the thread crest. The ramping region may comprise any number of thread revolutions. The number of thread revolutions in the ramping region does not have to be an integer; that is, the region could end with an incomplete revolution. In one embodiment, the ramping region comprises less than a full revolution of threading.

The bone screw and corresponding medical device may be made of any biocompatible material. In one embodiment, the bone screw and medical device are made of titanium alloy.

The bone screw is not limited to use with the devices described herein, and may be employed with any type of medical device. The medical device may have any number of bone screw holes.

What is claimed is:

1. A bone screw, comprising:
   a) a screw head;
   b) a smooth cylindrical shaft region, wherein said smooth cylindrical shaft region is adjacent to said screw head and is unthreaded to disengage from a bone screw hole upon full insertion;
   c) a first cylindrical shaft region comprising external threading, said threading of said first cylindrical shaft region having a first pitch, a first crest width, and a first thread diameter larger than a diameter of said bone screw hole to engage with said bone screw hole, wherein said first crest width is adapted to resist shearing when engaging with said bone screw hole;
   d) a second cylindrical shaft region comprising external threading, said threading of said second cylindrical shaft region having a pitch that transitions over one to three revolutions from said first pitch to a second smaller pitch, having a crest width that transitions over said one to three revolutions from said first crest width to a second smaller crest width, and having a thread diameter substantially equal to said first thread diameter;

e) a tapered shaft region comprising external threading, said threading of said tapered shaft region having said second smaller pitch, said second smaller crest width, and a tapered thread diameter decreasing in diameter from said first thread diameter, said tapered shaft region further comprising at least one recessed flute; and f) a sharp tip.

2. The bone screw of claim 1, wherein said tip comprises no threading or fluting.

3. The bone screw of claim 1, wherein each of said threadings of said first and second cylindrical shaft regions and said tapered shaft region comprises a forward face and a backward face, and further wherein an angle between said forward face and a central axis of the bone screw is substantially constant throughout each of said threadings of said first and second cylindrical shaft regions and said tapered shaft region.

4. The bone screw of claim 3, wherein said angle is about 50 degrees to about 70 degrees.

5. The bone screw of claim 1, wherein each of said threadings of said first and second cylindrical shaft regions and said tapered shaft region comprises a forward face and a backward face, and further wherein an angle between said backward face and a central axis of the bone screw is substantially constant throughout each of said threadings of said first and second cylindrical shaft regions and said tapered shaft region.

6. The bone screw of claim 5, wherein said angle is about 80 degrees to about 100 degrees.

7. The bone screw of claim 1, further comprising a ramping region between said smooth cylindrical shaft region and said first cylindrical shaft region, wherein said ramping region comprises threading that progressively increases in depth from said smooth cylindrical shaft region to said first cylindrical shaft region, measured from an outer surface of said smooth cylindrical shaft region to a thread crest of said threading of said ramping region, from a first thread depth to a second larger thread depth.

8. The bone screw of claim 7, wherein said ramping region comprises less than one full revolution of threading.

9. The bone screw of claim 1, wherein each of said first thread diameter and said thread diameter of said second cylindrical shaft region is about 3.0 mm to about 5.0 mm.

10. The bone screw of claim 1, wherein said at least one recessed flute comprises three recessed flutes.

11. The bone screw of claim 10, wherein each of said flutes spans an angle of about 90 degrees.

12. The bone screw of claim 1, wherein said first pitch is about 5.0 mm to about 7.0 mm and said second smaller pitch is about 2.0 mm to about 4.0 mm.

13. The bone screw of claim 1, wherein said first crest width is about 0.3 mm to about 0.4 mm and said second smaller crest width is about 0.1 mm to about 0.2 mm.

14. The bone screw of claim 1, wherein shaft diameters of said smooth cylindrical shaft region and said first and second cylindrical shaft regions are substantially equal.

15. The bone screw of claim 1, wherein said screw head has a recessed portion for receiving a tool.

16. The bone screw of claim 1, wherein said bone screw is made of a titanium alloy.

17. The bone screw of claim 1, wherein at least a portion of each of said threadings of said first and second cylindrical shaft regions and said tapered shaft region is sized and shaped to engage with a bone screw hole in an anterior cervical plate.

18. The bone screw of claim 1, wherein at least a portion of said threading of said tapered shaft region has a thread diameter smaller than a bone screw hole in an anterior cervical plate and is adapted to fit through said bone screw hole without engaging said bone screw hole.

19. A bone screw for engaging with a bone screw hole in an anterior cervical plate, comprising:

a) a sharp tip;

b) a tapered shaft region comprising external threading, wherein a shaft diameter of said tapered shaft region increases in a direction away from said tip, wherein a diameter of at least a portion of said threading of said tapered shaft region is smaller than a diameter of said bone screw hole, and wherein said threading of said tapered shaft region has a first pitch and a first crest width;

c) a first cylindrical shaft region comprising external threading, wherein a shaft diameter of said first cylindrical shaft region is smaller than said diameter of said bone screw hole, wherein at least a portion of said threading of said first cylindrical shaft region is sized and shaped larger than said diameter of said bone screw hole to engage with said bone screw hole, wherein said threading of said first cylindrical shaft region has a second pitch greater than said first pitch and a second crest width larger than said first crest width, and wherein said second crest width is adapted to resist shearing when engaging with said bone screw hole;

d) a second cylindrical shaft region without external threading to disengage from said bone screw hole upon full insertion, wherein a shaft diameter of said second cylindrical shaft region is smaller than said diameter of said bone screw hole; and e) a screw head, wherein a diameter of said screw head is larger than said diameter of said bone screw hole.

20. The bone screw of claim 19, wherein said tip comprises no threading or fluting.

21. The bone screw of claim 19, wherein said threading of said first cylindrical shaft region comprises a forward face and a backward face, and further wherein an angle between said forward face and a central axis of the bone screw is substantially constant throughout said threading of said first cylindrical shaft region.

22. The bone screw of claim 21, wherein said angle is about 50 degrees to about 70 degrees.

23. The bone screw of claim 19, wherein said threading of said first cylindrical shaft region comprises a forward face and a backward face, and further wherein an angle between said backward face and a central axis of the bone screw is substantially constant throughout said threading of said first cylindrical shaft region.

24. The bone screw of claim 23, wherein said angle is about 80 degrees to about 100 degrees.

25. The bone screw of claim 19, further comprising a ramping region between said second cylindrical shaft region and said first cylindrical shaft region, wherein said ramping region comprises threading that progressively increases in depth from said second cylindrical shaft region to said first cylindrical shaft region, measured from an outer surface of said second cylindrical shaft region to a thread crest of said threading of said ramping region, from a first thread depth to a second larger thread depth.

26. The bone screw of claim 25, wherein said ramping region comprises less than one full revolution of threading.

27. The bone screw of claim 19, wherein a thread diameter of said threading of said first cylindrical shaft region, measured from one crest of said threading to an opposite crest of said threading, is substantially constant along said first cylindrical shaft region.

28. The bone screw of claim 27, wherein said thread diameter of said threading of said first cylindrical shaft region is about 3.0 mm to about 5.0 mm.

29. The bone screw of claim 19, wherein said tapered shaft region further comprises at least one recessed flute.

30. The bone screw of claim 29, wherein said at least one recessed flute comprises three recessed flutes.

31. The bone screw of claim 30, wherein each of said flutes spans an angle of about 90 degrees.

32. The bone screw of claim 19, wherein said shaft diameter of said first cylindrical shaft region is substantially equal to said shaft diameter of said second cylindrical shaft region.

33. The bone screw of claim 19, wherein said screw head has a recessed portion for receiving a tool.

34. The bone screw of claim 19, wherein said bone screw is made of a titanium alloy.

35. An anterior cervical plating system, comprising:
a) an anterior cervical plate, comprising at least one hole for receiving a bone screw;
b) a bone screw, comprising a head; a body, wherein an unthreaded body region of said body adjacent to said head is unthreaded to disengage from said at least one hole upon full insertion and the rest of said body comprises a cylindrical shaft region of said body having a first body diameter and a tapered shaft region having a tapered diameter decreasing from said first body diameter, wherein said cylindrical shaft region comprises external threading having a first pitch and a first crest width and said tapered shaft region comprises external threading having a second pitch smaller than said first pitch and a second crest width smaller than said first crest width; and a tip;
c) wherein a diameter of said head is larger than a diameter of said at least one hole, further wherein said first body diameter of said body is smaller than said diameter of said at least one hole, further wherein at least a portion of said external threading of said cylindrical shaft region has a diameter larger than said diameter of said at least one hole, and wherein at least another portion of said external threading of said tapered shaft region has a diameter smaller than said diameter of said at least one hole;
d) wherein said portion of said external threading of said cylindrical shaft region having said diameter larger than said diameter of said at least one hole engages with said at least one hole when said bone screw is rotated through said at least one hole, and wherein said first crest width is adapted to resist shearing when engaging with said at least one hole; and
e) wherein said unthreaded body region is positioned within said at least one hole when said bone screw has been fully inserted in said at least one hole.

* * * * *